(12) United States Patent
Morton

(10) Patent No.: US 9,429,530 B2
(45) Date of Patent: *Aug. 30, 2016

(54) SCANNING SYSTEMS

(71) Applicant: Rapiscan Systems, Inc., Torrance, CA (US)

(72) Inventor: Edward James Morton, Guidlford (GB)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/142,286

(22) Filed: Dec. 27, 2013

(65) Prior Publication Data

US 2014/0185771 A1 Jul. 3, 2014

Related U.S. Application Data

(63) Continuation of application No. 12/919,485, filed as application No. PCT/GB2009/000493 on Feb. 25, 2009, now Pat. No. 8,644,453.

(30) Foreign Application Priority Data

Feb. 28, 2008 (GB) .................................. 0803641.0

(51) Int. Cl.
*G01N 23/087* (2006.01)
*G01N 23/201* (2006.01)
*G01V 5/00* (2006.01)

(52) U.S. Cl.
CPC ........... *G01N 23/201* (2013.01); *G01V 5/0041* (2013.01)

(58) Field of Classification Search
CPC .. G01V 5/0041; A61B 6/482; G01N 23/087; G01T 1/242; G01T 1/24
USPC ...................................................... 378/86, 87
See application file for complete search history.

(56) References Cited

U.S. PATENT DOCUMENTS

| 2,831,123 | A | 4/1958 | Daly |
| 2,952,790 | A | 9/1960 | Steen |
| 3,146,349 | A | 8/1964 | Jordan |
| 3,239,706 | A | 3/1966 | Farrell et al. |

(Continued)

FOREIGN PATENT DOCUMENTS

| DE | 2729353 | 1/1979 |
| DE | 3214910 | 5/1983 |

(Continued)

OTHER PUBLICATIONS

US 5,987,079, 11/1999, Scott et al. (withdrawn).

(Continued)

*Primary Examiner* — David J Makiya
*Assistant Examiner* — Dani Fox
(74) *Attorney, Agent, or Firm* — Novel IP

(57) ABSTRACT

The present application discloses methods and systems for scanning an object. The scanning system provides a first detector region having a thickness of at least 2 mm and a second detector region having a thickness of at least 5 mm. The second detector region is arranged to receive radiation that has passed through the first detector region. The method includes irradiating the object with radiation having having a peak energy of at least 1 MeV, and detecting the first profile radiation after it has interacted with or passed through the object in order to provide information relating to the object.

17 Claims, 6 Drawing Sheets

(56) References Cited

U.S. PATENT DOCUMENTS

| | | |
|---|---|---|
| 3,275,831 A | 9/1966 | Martin |
| 3,458,026 A | 7/1969 | Lauzon et al. |
| 3,485,339 A | 12/1969 | Miller et al. |
| 3,766,387 A | 10/1973 | Heffan et al. |
| 3,768,645 A | 10/1973 | Conway et al. |
| 3,770,955 A | 11/1973 | Tomita et al. |
| 3,784,837 A | 1/1974 | Homstrom |
| RE28,544 E | 9/1975 | Stein et al. |
| 3,904,923 A | 9/1975 | Schwartz |
| 3,955,678 A | 5/1976 | Moyer |
| 3,980,889 A | 9/1976 | Haas et al. |
| 4,047,035 A | 9/1977 | Dennhoven et al. |
| 4,057,725 A | 11/1977 | Wagner |
| 4,105,922 A | 8/1978 | Lambert et al. |
| 4,139,771 A | 2/1979 | Dennhoven et al. |
| 4,149,081 A * | 4/1979 | Seppi .................. 378/5 |
| 4,210,811 A | 7/1980 | Dennhoven et al. |
| 4,216,499 A | 8/1980 | Kunze et al. |
| 4,228,353 A | 10/1980 | Johnson |
| 4,259,721 A | 3/1981 | Kuznia |
| 4,266,425 A | 5/1981 | Allport |
| 4,274,005 A | 6/1981 | Yamamura et al. |
| 4,340,816 A | 7/1982 | Schott |
| 4,352,021 A | 9/1982 | Boyd et al. |
| 4,366,382 A | 12/1982 | Kotowski |
| 4,430,568 A | 2/1984 | Yoshida et al. |
| 4,468,802 A | 8/1984 | Friedel |
| 4,511,799 A * | 4/1985 | Bjorkholm .............. 250/367 |
| 4,566,113 A | 1/1986 | Donges et al. |
| 4,599,740 A | 7/1986 | Cable |
| 4,626,688 A * | 12/1986 | Barnes .................. 250/361 R |
| 4,641,330 A | 2/1987 | Herwig et al. |
| 4,672,649 A | 6/1987 | Rutt |
| 4,675,890 A | 6/1987 | Plessis et al. |
| 4,709,382 A * | 11/1987 | Sones .................. 378/62 |
| 4,736,401 A | 4/1988 | Donges et al. |
| 4,788,704 A | 11/1988 | Donges et al. |
| 4,809,857 A | 3/1989 | Steuck et al. |
| 4,817,123 A | 3/1989 | Sones et al. |
| 4,825,454 A | 4/1989 | Annis et al. |
| RE32,961 E | 6/1989 | Wagner |
| 4,866,439 A | 9/1989 | Kraus |
| 4,866,745 A | 9/1989 | Akai |
| 4,868,856 A | 9/1989 | Frith et al. |
| 4,872,188 A * | 10/1989 | Lauro et al. .................. 378/62 |
| 4,884,289 A | 11/1989 | Glockmann et al. |
| 4,887,604 A | 12/1989 | Shefer et al. |
| 4,963,746 A * | 10/1990 | Morgan et al. .......... 250/363.02 |
| 4,979,137 A | 12/1990 | Gerstenfeld et al. |
| 4,979,202 A | 12/1990 | Siczek et al. |
| 4,987,584 A | 1/1991 | Doenges |
| 4,991,189 A | 2/1991 | Boomgaarden et al. |
| 4,991,708 A | 2/1991 | Francioni |
| 5,022,062 A | 6/1991 | Annis |
| 5,033,106 A | 7/1991 | Kita |
| 5,065,418 A | 11/1991 | Bermbach et al. |
| 5,086,300 A | 2/1992 | Ashmore |
| 5,091,924 A | 2/1992 | Bermbach et al. |
| 5,092,451 A | 3/1992 | Jones et al. |
| 5,097,939 A | 3/1992 | Shanklin et al. |
| 5,098,640 A | 3/1992 | Gozani et al. |
| 5,138,167 A * | 8/1992 | Barnes .................. 250/370.01 |
| 5,144,191 A | 9/1992 | Jones et al. |
| 5,179,581 A | 1/1993 | Annis |
| 5,181,234 A | 1/1993 | Smith |
| 5,182,764 A | 1/1993 | Peschmann et al. |
| 5,221,843 A | 6/1993 | Alvarez |
| 5,224,144 A | 6/1993 | Annis |
| 5,237,598 A | 8/1993 | Albert |
| 5,243,693 A | 9/1993 | Maron |
| 5,247,556 A | 9/1993 | Eckert et al. |
| 5,247,561 A | 9/1993 | Kotowski |
| 5,253,283 A | 10/1993 | Annis et al. |
| 5,259,014 A | 11/1993 | Brettschneider |
| 5,272,627 A | 12/1993 | Maschhoff et al. |
| 5,313,511 A | 5/1994 | Annis et al. |
| 5,319,547 A | 6/1994 | Krug et al. |
| 5,341,916 A | 8/1994 | Doane et al. |
| 5,367,552 A | 11/1994 | Peschmann |
| 5,379,334 A | 1/1995 | Zimmer et al. |
| 5,410,156 A | 4/1995 | Miller |
| 5,412,702 A | 5/1995 | Sata |
| 5,467,377 A | 11/1995 | Dawson |
| 5,490,196 A | 2/1996 | Rudich et al. |
| 5,490,218 A | 2/1996 | Krug et al. |
| 5,493,596 A | 2/1996 | Annis |
| 5,505,291 A | 4/1996 | Huang et al. |
| 5,511,104 A | 4/1996 | Mueller et al. |
| 5,524,133 A | 6/1996 | Neale |
| 5,548,123 A * | 8/1996 | Perez-Mendez et al. .................. 250/370.11 |
| 5,557,108 A | 9/1996 | Tumer |
| 5,590,057 A | 12/1996 | Fletcher et al. |
| 5,600,303 A | 2/1997 | Husseiny et al. |
| 5,600,700 A | 2/1997 | Krug et al. |
| 5,604,778 A | 2/1997 | Polacin et al. |
| 5,606,167 A | 2/1997 | Miller |
| 5,633,907 A | 5/1997 | Gravelle et al. |
| 5,634,551 A | 6/1997 | Francioni et al. |
| 5,638,420 A | 6/1997 | Armistead |
| 5,642,393 A | 6/1997 | Krug et al. |
| 5,642,394 A | 6/1997 | Rothschild |
| 5,660,549 A | 8/1997 | Witt, III |
| 5,661,774 A | 8/1997 | Gordon et al. |
| 5,666,393 A | 9/1997 | Annis |
| 5,687,210 A | 11/1997 | Maitrejean et al. |
| 5,689,541 A | 11/1997 | Schardt |
| 5,692,028 A | 11/1997 | Geus et al. |
| 5,712,926 A | 1/1998 | Eberhard |
| 5,738,202 A | 4/1998 | Ydoate et al. |
| 5,751,837 A | 5/1998 | Watanabe et al. |
| 5,764,683 A | 6/1998 | Swift et al. |
| 5,768,334 A | 6/1998 | Maitrejean et al. |
| 5,787,145 A | 7/1998 | Geus |
| 5,796,802 A | 8/1998 | Gordon |
| 5,805,660 A | 9/1998 | Perion et al. |
| 5,818,897 A | 10/1998 | Gordon |
| 5,838,758 A | 11/1998 | Krug et al. |
| 5,838,759 A | 11/1998 | Armistead |
| 5,841,831 A | 11/1998 | Hell et al. |
| 5,859,891 A | 1/1999 | Hibbard |
| 5,870,449 A | 2/1999 | Lee et al. |
| 5,881,122 A | 3/1999 | Crawford et al. |
| 5,882,206 A | 3/1999 | Gillio |
| 5,887,047 A | 3/1999 | Bailey et al. |
| 5,901,198 A | 5/1999 | Crawford et al. |
| 5,903,623 A | 5/1999 | Swift et al. |
| 5,905,806 A | 5/1999 | Eberhard et al. |
| 5,909,477 A | 6/1999 | Crawford et al. |
| 5,910,973 A | 6/1999 | Grodzins |
| 5,930,326 A | 7/1999 | Rothschild et al. |
| 5,940,468 A | 8/1999 | Huang et al. |
| 5,949,842 A | 9/1999 | Schafer et al. |
| 5,963,211 A | 10/1999 | Oikawa et al. |
| 5,966,422 A | 10/1999 | Dafni et al. |
| 5,974,111 A | 10/1999 | Krug et al. |
| 5,982,843 A | 11/1999 | Bailey et al. |
| 5,987,097 A | 11/1999 | Salasoo |
| 6,018,562 A | 1/2000 | Willson |
| 6,021,174 A | 2/2000 | Campbell |
| 6,026,143 A | 2/2000 | Simanovsky et al. |
| 6,026,171 A | 2/2000 | Hiraoglu et al. |
| 6,031,890 A | 2/2000 | Bermbach et al. |
| 6,035,014 A | 3/2000 | Hiraoglu et al. |
| 6,037,597 A | 3/2000 | Karavolos |
| 6,044,353 A | 3/2000 | Pugliese, III |
| 6,058,158 A | 5/2000 | Eiler |
| 6,067,344 A | 5/2000 | Grodzins et al. |
| 6,067,366 A | 5/2000 | Simanovsky et al. |
| 6,073,751 A | 6/2000 | Worzischek |
| 6,075,871 A | 6/2000 | Simanovsky et al. |
| 6,076,400 A | 6/2000 | Bechwati et al. |
| 6,078,642 A | 6/2000 | Simanovsky et al. |
| 6,081,580 A | 6/2000 | Grodzins et al. |

(56) References Cited

U.S. PATENT DOCUMENTS

| | | |
|---|---|---|
| 6,088,423 A | 7/2000 | Krug et al. |
| 6,091,795 A | 7/2000 | Schafer et al. |
| 6,094,472 A | 7/2000 | Smith |
| 6,108,396 A | 8/2000 | Bechwati et al. |
| 6,111,974 A | 8/2000 | Hiraoglu et al. |
| 6,118,852 A | 9/2000 | Rogers et al. |
| 6,122,343 A | 9/2000 | Pidcock |
| 6,128,365 A | 10/2000 | Bechwati et al. |
| 6,137,895 A | 10/2000 | Al-sheikh |
| 6,149,592 A | 11/2000 | Yanof et al. |
| 6,151,381 A | 11/2000 | Grodzins et al. |
| 6,163,591 A | 12/2000 | Benjamin |
| 6,181,765 B1 | 1/2001 | Sribar et al. |
| 6,183,139 B1 | 2/2001 | Solomon et al. |
| 6,185,272 B1 | 2/2001 | Hiraoglu et al. |
| 6,188,745 B1 | 2/2001 | Gordon |
| 6,188,747 B1 | 2/2001 | Geus et al. |
| 6,192,101 B1 | 2/2001 | Grodzins et al. |
| 6,192,104 B1 | 2/2001 | Adams |
| 6,195,413 B1 | 2/2001 | Geus et al. |
| 6,195,444 B1 | 2/2001 | Simanovsky et al. |
| 6,198,795 B1 | 3/2001 | Naumann et al. |
| 6,216,540 B1 | 4/2001 | Nelson et al. |
| 6,218,943 B1 | 4/2001 | Ellenbogen |
| 6,236,709 B1 | 5/2001 | Perry et al. |
| 6,246,320 B1 | 6/2001 | Monroe |
| 6,249,567 B1 | 6/2001 | Rothschild et al. |
| 6,252,929 B1 | 6/2001 | Swift et al. |
| 6,256,369 B1 | 7/2001 | Lai |
| 6,256,404 B1 | 7/2001 | Gordon et al. |
| 6,269,142 B1 | 7/2001 | Smith |
| 6,272,230 B1 | 8/2001 | Hiraoglu et al. |
| 6,278,115 B1 | 8/2001 | Annis et al. |
| 6,282,260 B1 | 8/2001 | Grodzins |
| 6,292,533 B1 | 9/2001 | Swift et al. |
| 6,301,326 B2 | 10/2001 | Bjorkholm |
| 6,301,327 B1 | 10/2001 | Martens et al. |
| 6,304,629 B1 | 10/2001 | Conway et al. |
| 6,317,509 B1 | 11/2001 | Simanovsky et al. |
| 6,320,933 B1 | 11/2001 | Grodzins et al. |
| 6,324,249 B1 | 11/2001 | Fazzio |
| 6,345,113 B1 | 2/2002 | Crawford et al. |
| 6,347,132 B1 | 2/2002 | Annis |
| 6,356,620 B1 | 3/2002 | Rothschild et al. |
| 6,396,899 B2 | 5/2002 | Kuwabara |
| 6,418,189 B1 | 7/2002 | Schafer |
| 6,424,695 B1 | 7/2002 | Grodzins et al. |
| 6,429,578 B1 | 8/2002 | Danielsson et al. |
| 6,430,255 B2 | 8/2002 | Fenkart et al. |
| 6,431,344 B1 | 8/2002 | Emmermann et al. |
| 6,434,219 B1 | 8/2002 | Rothschild et al. |
| 6,435,715 B1 | 8/2002 | Betz et al. |
| 6,442,233 B1 | 8/2002 | Grodzins et al. |
| 6,445,765 B1 | 9/2002 | Frank et al. |
| 6,446,782 B1 | 9/2002 | Patrick |
| 6,453,003 B1 | 9/2002 | Springer et al. |
| 6,453,007 B2 | 9/2002 | Adams et al. |
| 6,456,684 B1 | 9/2002 | Mun et al. |
| 6,459,755 B1 | 10/2002 | Li |
| 6,459,761 B1 | 10/2002 | Grodzins et al. |
| 6,459,764 B1 | 10/2002 | Chalmers et al. |
| 6,473,487 B1 | 10/2002 | Le |
| RE37,899 E | 11/2002 | Grodzins et al. |
| 6,483,894 B2 | 11/2002 | Hartick et al. |
| 6,507,025 B1 | 1/2003 | Verbinski et al. |
| 6,528,787 B2 | 3/2003 | Katagami et al. |
| 6,532,276 B1 | 3/2003 | Hartick et al. |
| 6,542,574 B2 | 4/2003 | Grodzins |
| 6,542,578 B2 | 4/2003 | Ries et al. |
| 6,542,580 B1 | 4/2003 | Carver et al. |
| 6,546,072 B1 | 4/2003 | Chalmers |
| 6,552,346 B2 | 4/2003 | Verbinski et al. |
| 6,556,653 B2 | 4/2003 | Hussein |
| 6,563,903 B2 | 5/2003 | Kang et al. |
| 6,563,906 B2 | 5/2003 | Hussein et al. |
| 6,580,778 B2 | 6/2003 | Meder |
| 6,584,170 B2 | 6/2003 | Aust et al. |
| 6,590,956 B2 | 7/2003 | Fenkart et al. |
| 6,591,130 B2 | 7/2003 | Shahidi |
| 6,597,760 B2 | 7/2003 | Beneke et al. |
| 6,606,516 B2 | 8/2003 | Levine |
| 6,618,466 B1 | 9/2003 | Ning |
| 6,629,593 B2 | 10/2003 | Zeitler |
| 6,636,581 B2 | 10/2003 | Sorenson |
| 6,636,623 B2 | 10/2003 | Nelson et al. |
| 6,647,091 B2 | 11/2003 | Fenkart et al. |
| 6,647,094 B2 | 11/2003 | Harding et al. |
| 6,647,095 B2 | 11/2003 | Hsieh |
| 6,653,588 B1 | 11/2003 | Gillard-Hickman |
| 6,658,087 B2 | 12/2003 | Chalmers et al. |
| 6,661,876 B2 | 12/2003 | Turner et al. |
| 6,663,280 B2 | 12/2003 | Doenges |
| 6,665,373 B1 | 12/2003 | Kotowski et al. |
| 6,665,433 B2 | 12/2003 | Roder |
| 6,687,333 B2 | 2/2004 | Carroll et al. |
| 6,690,766 B2 | 2/2004 | Kresse |
| 6,707,879 B2 | 3/2004 | Mcclelland et al. |
| 6,715,533 B2 | 4/2004 | Kresse |
| 6,721,387 B1 | 4/2004 | Naidu et al. |
| 6,721,391 B2 | 4/2004 | McClelland et al. |
| 6,735,271 B1 | 5/2004 | Rand et al. |
| 6,737,652 B2 | 5/2004 | Lanza et al. |
| 6,748,043 B1 | 6/2004 | Dobbs |
| 6,754,298 B2 | 6/2004 | Fessler |
| 6,760,407 B2 | 7/2004 | Price et al. |
| 6,763,635 B1 | 7/2004 | Lowman |
| 6,770,884 B2 | 8/2004 | Bryman |
| 6,775,348 B2 | 8/2004 | Hoffman |
| 6,785,357 B2 | 8/2004 | Bernardi et al. |
| 6,788,761 B2 | 9/2004 | Bijjani et al. |
| 6,812,426 B1 | 11/2004 | Kotowski et al. |
| 6,813,374 B1 | 11/2004 | Karimi et al. |
| 6,816,571 B2 | 11/2004 | Bijjani et al. |
| 6,827,265 B2 | 12/2004 | Knowles et al. |
| 6,829,585 B1 | 12/2004 | Grewal et al. |
| 6,830,185 B2 | 12/2004 | Tsikos et al. |
| 6,837,422 B1 | 1/2005 | Meder |
| 6,837,432 B2 | 1/2005 | Tsikos et al. |
| 6,839,403 B1 | 1/2005 | Kotowski et al. |
| 6,843,599 B2 | 1/2005 | Le et al. |
| 6,856,667 B2 | 2/2005 | Ellengogen |
| 6,859,514 B2 | 2/2005 | Hoffman |
| 6,876,724 B2 | 4/2005 | Zhou et al. |
| 6,899,540 B1 | 5/2005 | Neiderman et al. |
| 6,901,135 B2 | 5/2005 | Fox et al. |
| 6,901,346 B2 | 5/2005 | Tracy et al. |
| 6,906,329 B2 | 6/2005 | Bryman |
| 6,907,101 B2 | 6/2005 | Hoffman |
| 6,920,197 B2 | 7/2005 | Kang et al. |
| 6,922,455 B2 | 7/2005 | Jurczyk et al. |
| 6,922,460 B2 | 7/2005 | Skatter et al. |
| 6,922,461 B2 | 7/2005 | Kang et al. |
| 6,928,141 B2 | 8/2005 | Carver et al. |
| 6,933,504 B2 | 8/2005 | Hoffman et al. |
| 6,934,354 B2 | 8/2005 | Hoffman |
| 6,940,071 B2 | 9/2005 | Ramsden et al. |
| 6,944,264 B2 | 9/2005 | Bijjani et al. |
| 6,947,517 B2 | 9/2005 | Hoffman |
| 6,950,492 B2 | 9/2005 | Besson |
| 6,950,493 B2 | 9/2005 | Besson |
| 6,952,163 B2 | 10/2005 | Huey et al. |
| 6,953,935 B1 | 10/2005 | Hoffman |
| 6,957,913 B2 | 10/2005 | Renkart et al. |
| 6,962,289 B2 | 11/2005 | Vatan et al. |
| 6,968,030 B2 | 11/2005 | Hoffman |
| 6,968,034 B2 | 11/2005 | Ellengogen |
| 6,971,577 B2 | 12/2005 | Tsikos et al. |
| 6,973,158 B2 | 12/2005 | Besson |
| 6,975,698 B2 | 12/2005 | Katcha et al. |
| 6,978,936 B2 | 12/2005 | Tsikos et al. |
| 6,980,627 B2 | 12/2005 | Qiu et al. |
| 6,990,171 B2 | 1/2006 | Toth et al. |
| 6,990,172 B2 | 1/2006 | Toth et al. |
| 6,991,371 B2 | 1/2006 | Georgeson et al. |

(56) References Cited

U.S. PATENT DOCUMENTS

| | | |
|---|---|---|
| 6,993,115 B2 | 1/2006 | Mcguire et al. |
| 6,996,209 B2 | 2/2006 | Marek |
| 7,010,083 B2 | 3/2006 | Hoffman |
| 7,016,459 B2 | 3/2006 | Ellenbogen et al. |
| 7,020,241 B2 | 3/2006 | Beneke et al. |
| 7,020,242 B2 | 3/2006 | Ellenbogen |
| 7,023,956 B2 | 4/2006 | Heaton et al. |
| 7,023,957 B2 | 4/2006 | Bijjani et al. |
| 7,027,553 B2 | 4/2006 | Dunham et al. |
| 7,027,554 B2 | 4/2006 | Gaultier et al. |
| 7,031,430 B2 | 4/2006 | Kaucic, Jr. et al. |
| 7,031,434 B1 | 4/2006 | Saunders et al. |
| 7,034,313 B2 | 4/2006 | Hoffman |
| 7,039,154 B1 | 5/2006 | Ellenbogen et al. |
| 7,039,159 B2 | 5/2006 | Muenchau et al. |
| 7,042,975 B2 | 5/2006 | Heuscher |
| 7,045,787 B1 | 5/2006 | Verbinski et al. |
| 7,046,756 B2 | 5/2006 | Hoffman |
| 7,046,761 B2 | 5/2006 | Ellenbogen et al. |
| 7,046,768 B1 | 5/2006 | Gilevich |
| 7,050,536 B1 | 5/2006 | Fenkart et al. |
| 7,050,541 B2 | 5/2006 | Bittl |
| 7,054,408 B2 | 5/2006 | Jiang et al. |
| 7,062,009 B2 | 6/2006 | Karimi et al. |
| 7,062,011 B1 | 6/2006 | Tybinkowski et al. |
| 7,062,074 B1 | 6/2006 | Beneke |
| 7,064,334 B2 | 6/2006 | Hoffman et al. |
| 7,065,175 B2 | 6/2006 | Green |
| 7,065,179 B2 | 6/2006 | Block et al. |
| 7,068,749 B2 | 6/2006 | Kollegal et al. |
| 7,068,750 B2 | 6/2006 | Toth et al. |
| 7,068,751 B2 | 6/2006 | Toth et al. |
| 7,072,434 B1 | 7/2006 | Tybinkowski et al. |
| 7,076,029 B2 | 7/2006 | Toth et al. |
| 7,078,699 B2 | 7/2006 | Seppi |
| 7,081,628 B2 | 7/2006 | Granfors et al. |
| 7,084,404 B2 | 8/2006 | Hoffman et al. |
| 7,087,902 B2 | 8/2006 | Wang et al. |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,099,434 B2 | 8/2006 | Adams et al. |
| 7,099,435 B2 | 8/2006 | Heumann et al. |
| 7,103,137 B2 | 9/2006 | Seppi et al. |
| 7,110,488 B2 | 9/2006 | Katcha et al. |
| 7,112,797 B2 | 9/2006 | Hoge |
| 7,116,749 B2 | 10/2006 | Besson |
| 7,116,751 B2 | 10/2006 | Ellenbogen et al. |
| 7,119,553 B2 | 10/2006 | Yang et al. |
| 7,123,681 B2 | 10/2006 | Ellenbogen et al. |
| 7,127,027 B2 | 10/2006 | Hoffman |
| 7,130,374 B1 | 10/2006 | Jacobs et al. |
| 7,133,491 B2 | 11/2006 | Bernardi et al. |
| 7,136,450 B2 | 11/2006 | Ying et al. |
| 7,136,451 B2 | 11/2006 | Naidu et al. |
| 7,139,367 B1 | 11/2006 | Le |
| 7,139,406 B2 | 11/2006 | Mcclelland et al. |
| 7,142,208 B2 | 11/2006 | Lorenz |
| 7,142,629 B2 | 11/2006 | Edie et al. |
| 7,149,278 B2 | 12/2006 | Arenson et al. |
| 7,149,339 B2 | 12/2006 | Veneruso |
| 7,155,812 B1 | 1/2007 | Peterson et al. |
| 7,158,611 B2 | 1/2007 | Heismann et al. |
| 7,162,285 B2 | 1/2007 | Owens et al. |
| 7,164,747 B2 | 1/2007 | Ellenbogen et al. |
| 7,164,750 B2 | 1/2007 | Nabors et al. |
| 7,166,458 B2 | 1/2007 | Ballerstadt et al. |
| 7,166,844 B1 | 1/2007 | Gormley et al. |
| 7,167,539 B1 | 1/2007 | Hoffman |
| 7,173,998 B2 | 2/2007 | Hoffman et al. |
| 7,177,387 B2 | 2/2007 | Yasunaga et al. |
| 7,177,391 B2 | 2/2007 | Chapin et al. |
| 7,187,756 B2 | 3/2007 | Gohno et al. |
| 7,190,757 B2 | 3/2007 | Ying et al. |
| 7,192,031 B2 | 3/2007 | Dunham et al. |
| 7,197,113 B1 | 3/2007 | Katcha et al. |
| 7,197,172 B1 | 3/2007 | Naidu et al. |
| 7,203,629 B2 | 4/2007 | Ozis et al. |
| 7,204,125 B2 | 4/2007 | Fine et al. |
| 7,206,379 B2 | 4/2007 | Lemaitre |
| 7,207,713 B2 | 4/2007 | Lowman |
| 7,212,113 B2 | 5/2007 | Zanovitch |
| 7,215,731 B1 | 5/2007 | Basu et al. |
| 7,215,737 B2 | 5/2007 | Li et al. |
| 7,215,738 B2 | 5/2007 | Muenchau et al. |
| 7,218,700 B2 | 5/2007 | Huber et al. |
| 7,218,704 B1 | 5/2007 | Adams et al. |
| 7,224,763 B2 | 5/2007 | Naidu et al. |
| 7,224,765 B2 | 5/2007 | Ellenbogen |
| 7,224,766 B2 | 5/2007 | Jiang et al. |
| 7,224,769 B2 | 5/2007 | Turner |
| 7,233,640 B2 | 6/2007 | Ikhlef et al. |
| 7,236,564 B2 | 6/2007 | Hopkins et al. |
| 7,238,945 B2 | 7/2007 | Hoffman et al. |
| 7,247,856 B2 | 7/2007 | Hoge et al. |
| 7,251,310 B2 | 7/2007 | Smith |
| 7,257,189 B2 | 8/2007 | Modica et al. |
| 7,260,170 B2 | 8/2007 | Arenson et al. |
| 7,260,171 B1 | 8/2007 | Arenson et al. |
| 7,260,172 B2 | 8/2007 | Arenson et al. |
| 7,260,173 B2 | 8/2007 | Wakayama et al. |
| 7,260,174 B2 | 8/2007 | Hoffman et al. |
| 7,260,182 B2 | 8/2007 | Toth et al. |
| 7,260,255 B2 | 8/2007 | Polichar et al. |
| 7,263,160 B2 | 8/2007 | Schlomka et al. |
| 7,266,180 B1 | 9/2007 | Saunders et al. |
| 7,272,429 B2 | 9/2007 | Walker et al. |
| 7,274,767 B2 | 9/2007 | Clayton et al. |
| 7,277,577 B2 | 10/2007 | Ying et al. |
| 7,279,120 B2 | 10/2007 | Cheng et al. |
| 7,280,631 B2 | 10/2007 | De Man et al. |
| 7,282,727 B2 | 10/2007 | Retsky |
| 7,283,604 B2 | 10/2007 | De Man et al. |
| 7,283,609 B2 | 10/2007 | Possin et al. |
| 7,295,019 B2 | 11/2007 | Yang et al. |
| 7,295,651 B2 | 11/2007 | Delgado et al. |
| 7,298,812 B2 | 11/2007 | Tkaczyk et al. |
| 7,302,083 B2 | 11/2007 | Larson et al. |
| 7,308,073 B2 | 12/2007 | Tkaczyk et al. |
| 7,308,074 B2 | 12/2007 | Jiang et al. |
| 7,308,077 B2 | 12/2007 | Bijjani et al. |
| 7,317,195 B2 | 1/2008 | Eikman |
| 7,317,259 B2 | 1/2008 | Yamauchi |
| 7,317,390 B2 | 1/2008 | Huey et al. |
| 7,319,737 B2 | 1/2008 | Singh |
| 7,322,745 B2 | 1/2008 | Agrawal et al. |
| 7,324,625 B2 | 1/2008 | Eilbert |
| 7,327,853 B2 | 2/2008 | Ying et al. |
| 7,330,527 B2 | 2/2008 | Hoffman et al. |
| 7,330,535 B2 | 2/2008 | Arenson et al. |
| 7,333,587 B2 | 2/2008 | De Man et al. |
| 7,333,588 B2 | 2/2008 | Mistretta et al. |
| 7,333,589 B2 | 2/2008 | Ellenbogen et al. |
| 7,335,887 B1 | 2/2008 | Verbinski et al. |
| 7,336,769 B2 | 2/2008 | Arenson et al. |
| 7,349,525 B2 | 3/2008 | Morton et al. |
| 7,352,843 B2 | 4/2008 | Hu et al. |
| 7,356,174 B2 | 4/2008 | Leue et al. |
| 7,369,640 B2 | 5/2008 | Seppi et al. |
| 7,386,092 B2 | 6/2008 | Kang et al. |
| 7,397,891 B2 | 7/2008 | Johnson et al. |
| 7,420,174 B2 | 9/2008 | Kurita et al. |
| 7,429,738 B2 | 9/2008 | Li et al. |
| 7,440,543 B2 | 10/2008 | Morton |
| 7,460,639 B2 | 12/2008 | Tudor et al. |
| 7,470,914 B2 | 12/2008 | Li et al. |
| 7,475,428 B2 | 1/2009 | Smith et al. |
| 7,475,866 B2 | 1/2009 | Hu et al. |
| 7,483,510 B2 | 1/2009 | Carver et al. |
| 7,483,511 B2 | 1/2009 | Bendahan et al. |
| 7,492,855 B2 | 2/2009 | Hopkins et al. |
| 7,500,931 B2 | 3/2009 | Rosemeier et al. |
| 7,505,556 B2 | 3/2009 | Chalmers et al. |

(56) References Cited

U.S. PATENT DOCUMENTS

| | | | |
|---|---|---|---|
| 7,505,557 B2 | 3/2009 | Modica et al. | |
| 7,512,215 B2 | 3/2009 | Morton et al. | |
| 7,564,939 B2 | 7/2009 | Morton et al. | |
| 7,580,505 B2 | 8/2009 | Kang et al. | |
| 7,649,976 B2 | 1/2010 | Georgeson et al. | |
| 7,663,109 B2 | 2/2010 | Kang et al. | |
| 7,684,538 B2 | 3/2010 | Morton et al. | |
| 7,724,869 B2 | 5/2010 | Wang et al. | |
| 7,734,066 B2 | 6/2010 | DeLia et al. | |
| 7,738,687 B2 | 6/2010 | Tortora et al. | |
| 7,742,568 B2 | 6/2010 | Smith | |
| 7,762,760 B2 | 7/2010 | Takehara et al. | |
| 7,783,003 B2 | 8/2010 | Clayton et al. | |
| 7,809,104 B2 | 10/2010 | Foland | |
| 7,817,775 B2 | 10/2010 | Kang et al. | |
| 7,835,486 B2 | 11/2010 | Basu et al. | |
| 7,876,879 B2 | 1/2011 | Morton | |
| 7,885,375 B2 | 2/2011 | Bernard De Man et al. | |
| 7,903,783 B2 | 3/2011 | Modica et al. | |
| 7,973,697 B2 | 7/2011 | Reilly et al. | |
| 7,991,117 B2 | 8/2011 | Chen et al. | |
| 8,031,903 B2 | 10/2011 | Paresi et al. | |
| 8,173,970 B2 | 5/2012 | Inbar | |
| 8,263,938 B2 | 9/2012 | Bjorkholm | |
| 8,350,747 B2 | 1/2013 | Delia et al. | |
| 8,498,376 B2 | 7/2013 | Modica et al. | |
| 8,502,699 B2 | 8/2013 | Zerwekh et al. | |
| 8,644,453 B2 * | 2/2014 | Morton | 378/86 |
| 8,668,386 B2 | 3/2014 | Morton et al. | |
| 8,744,033 B2 | 6/2014 | Oosaka et al. | |
| 2002/0031202 A1 | 3/2002 | Callerame et al. | |
| 2002/0038753 A1 | 4/2002 | Ursu | |
| 2002/0045152 A1 | 4/2002 | Viscardi et al. | |
| 2003/0023592 A1 | 1/2003 | Modica et al. | |
| 2003/0085163 A1 | 5/2003 | Chan et al. | |
| 2004/0017888 A1 | 1/2004 | Seppi | |
| 2004/0086078 A1 | 5/2004 | Adams | |
| 2004/0101098 A1 | 5/2004 | Bijjani et al. | |
| 2004/0125914 A1 | 7/2004 | Kang | |
| 2004/0141584 A1 | 7/2004 | Bernardi | |
| 2004/0213378 A1 | 10/2004 | Zhou et al. | |
| 2004/0258198 A1 | 12/2004 | Carver | |
| 2004/0258305 A1 | 12/2004 | Burnham et al. | |
| 2005/0008119 A1 | 1/2005 | McClelland et al. | |
| 2005/0031076 A1 | 2/2005 | McClelland et al. | |
| 2005/0117683 A1 | 6/2005 | Mishin et al. | |
| 2005/0117700 A1 | 6/2005 | Peschmann | |
| 2005/0156734 A1 | 7/2005 | Zerwekh | |
| 2005/0169421 A1 | 8/2005 | Muenchau | |
| 2005/0226364 A1 | 10/2005 | Bernard De Man et al. | |
| 2005/0251397 A1 | 11/2005 | Zanovitch et al. | |
| 2006/0011848 A1 * | 1/2006 | Rushbrooke et al. | 250/367 |
| 2006/0115109 A1 | 6/2006 | Whitson et al. | |
| 2006/0274916 A1 | 12/2006 | Chan et al. | |
| 2007/0110215 A1 | 5/2007 | Hu | |
| 2007/0172129 A1 | 7/2007 | Tortora | |
| 2007/0194909 A1 | 8/2007 | Garfield et al. | |
| 2007/0210255 A1 | 9/2007 | Bjorkholm | |
| 2007/0269005 A1 | 11/2007 | Chalmers | |
| 2007/0280416 A1 | 12/2007 | Bendahan et al. | |
| 2007/0280502 A1 | 12/2007 | Paresi | |
| 2008/0044801 A1 | 2/2008 | Modica | |
| 2008/0056432 A1 | 3/2008 | Pack et al. | |
| 2011/0176660 A1 | 7/2011 | Morton | |
| 2011/0216881 A1 | 9/2011 | Modica et al. | |

FOREIGN PATENT DOCUMENTS

| | | |
|---|---|---|
| EP | 0287707 | 11/1982 |
| EP | 0077018 | 4/1983 |
| EP | 176314 | 4/1986 |
| EP | 0176314 | 4/1986 |
| EP | 432568 | 6/1991 |
| EP | 531993 | 3/1993 |
| EP | 584871 | 3/1994 |
| EP | 919186 | 6/1999 |
| EP | 924742 | 6/1999 |
| EP | 930046 | 7/1999 |
| EP | 963925 | 12/1999 |
| EP | 1277439 | 1/2003 |
| EP | 1374776 | 1/2004 |
| EP | 1413898 | 4/2004 |
| EP | 2255224 | 9/2009 |
| FR | 2328280 | 5/1977 |
| GB | 1497396 | 1/1978 |
| GB | 1526041 | 9/1978 |
| GB | 2015245 | 9/1979 |
| GB | 2089109 | 6/1982 |
| GB | 2212903 | 8/1989 |
| GB | 2255634 | 11/1992 |
| GB | 2337032 | 11/1999 |
| GB | 2404431 | 2/2005 |
| GB | 2409268 A | 6/2005 |
| GB | 2424065 | 9/2006 |
| GB | 2437777 | 11/2007 |
| GB | 2438317 | 11/2007 |
| GB | 2470161 | 11/2010 |
| GB | 2470330 | 11/2010 |
| GB | 2470163 | 9/2012 |
| JP | 570175247 | 10/1982 |
| JP | 59016254 | 1/1984 |
| JP | 5975549 | 4/1984 |
| JP | 600015546 | 1/1985 |
| JP | 600021440 | 2/1985 |
| JP | 10211196 | 8/1998 |
| JP | 11230918 | 8/1999 |
| JP | 2001176408 | 6/2001 |
| JP | 2001233440 | 8/2001 |
| JP | 2003126075 | 5/2003 |
| JP | 2004000605 | 1/2004 |
| JP | 2005013768 | 1/2005 |
| WO | 9528715 | 10/1995 |
| WO | 9855851 | 10/1998 |
| WO | 9960387 | 11/1999 |
| WO | 03051201 | 6/2003 |
| WO | 03105159 | 12/2003 |
| WO | 2004010127 | 1/2004 |
| WO | 2004037088 | 5/2004 |
| WO | 2004411625 | 12/2004 |
| WO | 2005084351 | 9/2005 |
| WO | 2005091227 | 9/2005 |
| WO | 2005098400 | 10/2005 |
| WO | 2006036076 | 4/2006 |
| WO | 2006045019 | 4/2006 |
| WO | 2006078691 | 7/2006 |
| WO | 2006095188 | 9/2006 |
| WO | 2006135586 | 12/2006 |
| WO | 2007035359 | 3/2007 |
| WO | 2007051092 | 5/2007 |
| WO | 2007055720 | 5/2007 |
| WO | 2007068933 | 6/2007 |
| WO | 2007103216 | 9/2007 |
| WO | 2008017983 | 2/2008 |
| WO | 2009027667 | 3/2009 |
| WO | 2009106803 | 9/2009 |
| WO | 2009106815 | 9/2009 |
| WO | 2009106857 | 9/2009 |

OTHER PUBLICATIONS

International Search Report for PCT/GB2009/001277, Jul. 20, 2010, Rapiscan Systems Inc.
International Search Report for PCT/GB2009/001275, Jul. 24, 2009, Rapiscan Security Products Inc.
International Search Report for PCT/GB2009/001250, Mar. 2, 2010, Rapiscan Security Products Inc.
International Search Report for PCT/GB2009/000575, Apr. 7, 2010, Rapiscan Security Products Inc.
International Search Report for PCT/GB2004/001747, Aug 10, 2004, CXR Ltd.
International Search Report for PCT/US2007/005444, Oct. 29, 2007, Telesecurity Sciences, Inc.
International Search Report for PCT/US2006/11492, Oct. 11, 2007, United Technologies Corporation.

(56) References Cited

OTHER PUBLICATIONS

International Search Report for PCT/US2012/024182, Aug. 20, 2012, Rapiscan Systems Inc.
International Preliminary Report on Patentability for PCT/US2012/024182, Aug. 13, 2013, Rapiscan Systems Inc.
International Search Report for PCT/GB2009/000515, Apr. 15, 2010, Rapiscan Security Products, Inc.
International Search Report for PCT/GB2009/000497, Mar. 11, 2010, Rapiscan Security Products, Inc.
International Search Report for PCT/GB2009/001444, May 27, 2010, Rapiscan Security Products, Inc.
International Search Report for PCT/GB2009/000556, Apr. 15, 2010, Rapiscan Security Products, Inc.
"Mobile X-Ray Inspection Systems", Internet Citation, Feb. 12, 2007, pp. 1-2, URL: http://web.archive.org/web/20070212000928/http://www.bombdetection.com/cat_details.php?catid=20>.
Molchanov et al., "Nanosecond Gated Optical Sensors for Ocean Optic Applications", Sensors Applications Symposium, 2006, Proceedings of the 2006 IEEE, Feb. 7, 2006, pp. 147-150.

* cited by examiner

SCANNING SYSTEMS

CROSS REFERENCE

The present application is a national stage application of PCT/GB2009/000493, filed on Feb. 25, 2009, which further relies on Great Britain Patent Application Number 0803641.0, filed on Feb. 28, 2008, for priority.

FIELD OF THE INVENTION

The present invention relates to scanning systems. It has particular application in scanning systems for cargo, but can also be used in scanners for other applications such as security and high energy medical scanners.

BACKGROUND OF THE INVENTION

There is a requirement for screening of cargo for the purpose of identifying the presence of illicit materials and objects. Currently, such screening is often performed using X-ray scanners.

X-ray scanners for cargo inspection typically comprise a high energy X-ray source (usually based on an X-ray linear accelerator) with a beam quality of 4 MeV to 9 MeV. The X-ray output from the X-ray linear accelerator is then collimated down to a narrow fan-beam of radiation which is shone through the item of cargo under inspection. A linear array of X-ray detector elements is then positioned opposite to the X-ray source such that it is irradiated by the fan-beam of radiation after attenuation of the X-ray beam by the object under inspection.

SUMMARY OF THE INVENTION

An aspect of the invention comprises a scanning method for scanning an object comprising: providing a first detector region and a second detector region wherein the second detector region is arranged to receive radiation that has passed through the first detector region; irradiating the object with radiation having a first energy profile; detecting the first profile radiation after it has interacted with or passed through the object in order to provide information relating to the object, wherein detecting the first profile radiation comprises: detecting the first profile radiation at the first detector region; receiving the first profile radiation that has passed through the first detector region at the second detector region; detecting the first profile radiation at the second detector region; the scanning method further comprising: irradiating the object with radiation having a second energy profile, different to the first energy profile; detecting the second profile radiation after it has interacted with or passed through the object in order to provide information relating to the object, wherein detecting the second profile radiation comprises: detecting the second profile radiation at the first detector region; receiving the second profile radiation that has passed through the first detector region at the second detector region; detecting the second profile radiation at the second detector region.

In one embodiment, the present invention is a scanning method for scanning an object comprising: providing a first detector region having a thickness of at least 2 mm and a second detector region having a thickness of at least 5 mm wherein the second detector region is arranged to receive radiation that has passed through the first detector region; irradiating the object with radiation having a peak energy of at least 1 MeV; detecting the first profile radiation after it has interacted with or passed through the object in order to provide information relating to the object, wherein detecting the first profile radiation comprises a) detecting the first profile radiation at the first detector region, b) receiving the first profile radiation that has passed through the first detector region at the second detector region, and c) detecting the first profile radiation at the second detector region; the scanning method further comprising: x) irradiating the object with radiation having a second energy profile, relatively lower than the first energy profile, and having a peak energy of at least 0.5 MeV and y) detecting the second profile radiation after it has interacted with or passed through the object in order to provide information relating to the object, wherein detecting the second profile radiation comprises: i) detecting the second profile radiation at the first detector region; ii) receiving the second profile radiation that has passed through the first detector region at the second detector region; and iii) detecting the second profile radiation at the second detector region.

Optionally, the method comprises positioning the first detector region between the object and the second detector region. The method comprises determining information relating to the object based upon information from the first and second detector regions relating to the first and second energy profile radiation. The method comprises determining information by inputting the information from the first and second detector regions relating to the first and second energy profile radiation into a least squares minimization technique to obtain information relating to the object.

The method comprises calculating the ratio, $(A/B)_1/(A/B)_2$ in order to the determine information relating to the object based upon the calculated ratio, wherein A is indicative of the amount of radiation detected at the first detector region, B is indicative of the amount of radiation detected at the first detector region, $(A/B)_1$ is the ratio of first profile radiation detected at the first detector region relative to first profile radiation detected at the second detector region, and $(A/B)_2$ is the ratio of second profile radiation detected at the first detector region relative to second profile radiation detected at the second detector region.

The method comprises irradiating and detecting the first profile radiation before the second profile radiation, or vice versa, wherein irradiating the object comprises irradiating the object in discrete bursts. The method comprises sending detected information received in response to a burst from the detector regions before the next burst occurs.

The low energy profile radiation comprises 3 MeV x-ray radiation and the high energy profile radiation comprises 6 MeV x-ray radiation. The method comprises configuring the first detector region and the second detector region to detect a predetermined amount of radiation relative to each other.

The method comprises configuring the first detector region and the second detector region to detect substantially the same amount of radiation as each other.

The method comprises configuring any one or more of size, shape or material of each detector region so that the first detector region and the second detector region detect the predetermined amount of radiation relative to each other.

The method comprises providing a first detector including the first detector region and a second detector including the second detector region. The method comprises irradiating the object with radiation at more than two energy profiles, such as at three energy profiles or four energy profiles or five energy profiles or six energy profiles or seven energy profiles.

In another embodiment, the present invention is directed toward a method of scanning overlapping objects comprising using the method of claim 1 to determine information relating to each overlapping object in a region of the object which does not overlap another object and using the determined information to calculate a reference detection value or values relating to a value or values expected to be detected in the region in which the objects overlap in the absence of further objects that are not present outside the overlapping region and using the method of any preceding claim to ascertain information relating to the region in which the objects overlap and comparing the ascertained information to the expected values to determine whether an additional object is present within the region in which the objects overlap.

In another embodiment, the present invention is directed toward a scanning system for scanning an object comprising: a variable energy level radiation source arranged to irradiate an object with radiation having a plurality of different energy profiles including a first energy profile having a peak energy of at least 1 MeV and a second relatively lower energy profile having a peak energy of at least 0.5 MeV, a detector arrangement arranged to detect radiation after it has interacted with or passed through the object, wherein the detector arrangement comprises a first detector region having a thickness of at least 2 mm and arranged to detect radiation and a second detector region having a thickness of at least 5 mm and arranged to detect radiation wherein the second detector region is arranged to receive radiation that has passed through the first detector region.

The scanning system comprises a controller arranged to coordinate timing of irradiation events such that detected information obtained in response to an irradiation event is sent from the detector regions before the next event occurs. The first detector region is positioned between the object and the second detector region.

The scanning system comprises a controller arranged to determine information relating to the object based upon information from the first and second detector regions relating to the first and second energy profile radiation.

The controller is arranged to determine information by inputting the information from the first and second detector regions relating to the first and second energy profile radiation into a least squares minimization technique to obtain information relating to the object.

The controller is arranged to calculate the ratio, $(A/B)_1/(A/B)_2$ in order to the determine information relating to the object based upon the calculated ratio, wherein A is indicative of the amount of radiation detected at the first detector region, B is indicative of the amount of radiation detected at the first detector region, $(A/B)_1$ is the ratio of first profile radiation detected at the first detector region relative to first profile radiation detected at the second detector region, and $(A/B)_2$ is the ratio of second profile radiation detected at the first detector region relative to second profile radiation detected at the second detector region.

The scanning system comprises a plurality of detector arrays, each detector array comprising a first detector region and a second detector region. The scanning system comprises a concentrator and switch arranged to coherently relay gathered information from the detector regions. The first detector region and the second detector region are configured to detect substantially the same amount of radiation as each other.

The independent claims define aspects of the invention for which protection is sought. The dependent claims define preferable inventive features. Any of the features of the dependent claims may be used in combination with the features of other claims or other aspects of the invention, even if they are not explicitly dependent upon them—this will be clear to a person skilled in this field.

Where a feature is claimed in one category (e.g. method, system, detector arrangement, etc.) protection is sought for that feature in other categories even if not explicitly claimed.

BRIEF DESCRIPTION OF THE DRAWINGS

Embodiments of the invention will now be described, by way of example only, with reference to the accompanying drawings, in which.

DETAILED DESCRIPTION OF THE INVENTION

Figure 1:
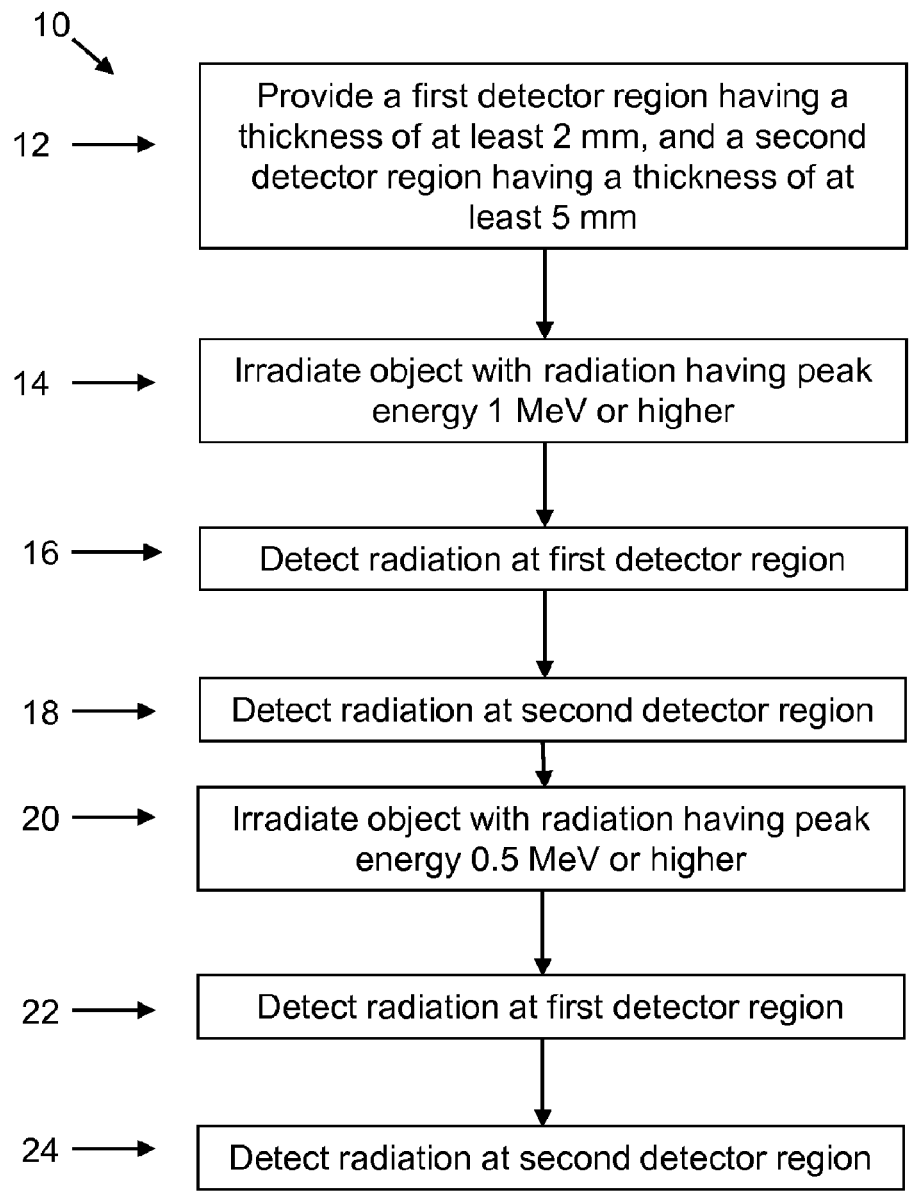
FIG. 1 is a flowchart outlining a method according to an embodiment of the invention.
Figure 2:
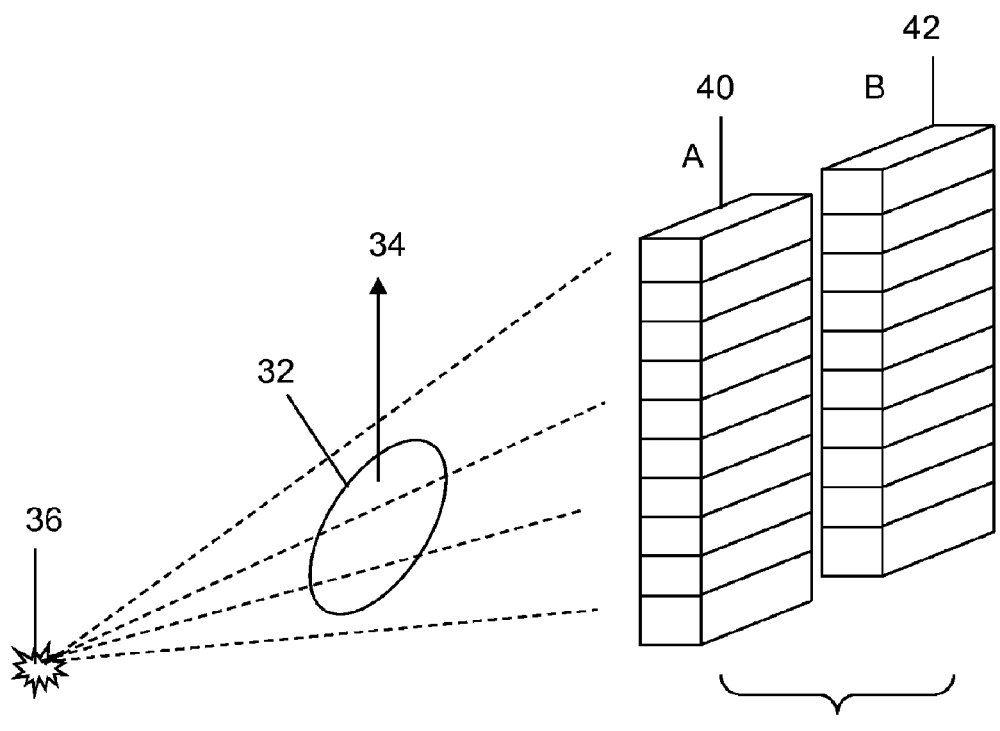
FIG. 2 schematically shows a scanning system according to an embodiment of the invention.

Referring to FIGS. 1 and 2, a method of the invention provides a method 10 and system 30 for scanning an object 32. The system 30 comprises a radiation source 36 arranged to irradiate the object 32 with radiation. In this embodiment, the source 36 is a switchable energy linear accelerator source. Other suitable sources will be apparent to the skilled person. In this embodiment the object 32 moves in the direction of arrow 34 through a scanning zone. The object 32 might be a lorry carrying cargo for example, driving through a scanning zone, which the source 36 is arranged to irradiate. In other embodiments, the object 32 might be stationary. The radiation source 36 is arranged to operate at at least two different levels. In this example, the source 36 is able to operate at a high level to provide radiation having a peak energy of at least 1 MeV and at a low level to provide radiation having a peak energy of at least 0.5 MeV. In this particular example the high level radiation has a peak value of 6 MeV, and the low level radiation has a peak value of 3 MeV. In this context peak value is the energy value at which the highest intensity of radiation is emitted by the source 36.

The scanning system 30 also comprises a detector arrangement 38. The detector arrangement is arranged to detect radiation after it has interacted with or passed through the object 32 in order to provide information to scan the object. The detector arrangement 38 comprises a first detector 40 and a second detector 42. The first detector 40 has a thickness of at least 2 mm. In this embodiment the thickness of the first detector is about 15 mm. In other embodiments the thickness may be more or less and can be tuned as required by a skilled person. The second detector 42 has a thickness of at least 5 mm. In this embodiment the thickness of the second detector 42 is about 30 mm. Once again, it will be clear to the skilled person that this detector thickness can be varied by experimentation in order to tune the detector arrangement 38 as required. For example, in some embodiments, the detectors may be tuned to detect the same amount of radiation as each other, to provide more efficient signal processing. In this embodiment, referring to FIG. 3, the first detector 40 is positioned between the object 32 and the second detector 42. In other embodiments, the skilled person may envisage a different arrangement. In this particular embodiment, this arrangement provides a simple geometry in order to achieve the desired detector configuration such that radiation passing through the first detector 40 reaches the second detector 42 after it has interacted with the object 32. In this embodiment, the detector arrangement 38 is a linear detector array with front 40, A, and rear 42, B, detectors.

The system 30 in its broadest embodiment does not include a movement sensor. In some embodiments, the system 30 includes a movement sensor (not shown). The movement sensor 44 is arranged to measure any one or more of the position, speed, velocity or acceleration of the object 32, and data gathered using the movement sensor may be used to coordinate timing of data capture as the object is scanned.

Referring to FIG. 1, the scanning method 10 comprises the step of providing 12 a first detector region having a thickness of at least 2 mm, and a second detector region having a thickness of at least 5 mm. The method 10 also comprises the steps of irradiating 14 an object to be scanned with radiation having a peak energy value of 1 MeV or more, detecting 16 radiation at the first detector region 40, and then detecting 18 radiation at the second detector region 42 (the second detector region is arranged to receive radiation that has passed through the first detector region). The method 10 comprises detecting the radiation after it has interacted with or passed through the object in order to provide information relating to the object.

The method 10 further comprises irradiating 20 the object with radiation having a peak energy value of 0.5 MeV or more (but less than the peak energy value of the energy irradiated at step 14), and again detecting 22 radiation at the first detector region 40, and then detecting 24 radiation at the second detector region 42.

In this example the object is scanned with higher energy profile radiation prior to scanning with lower energy profile radiation. In other embodiments, the object may be scanned with lower energy profile radiation prior to scanning with higher energy profile radiation. In yet further embodiments, there may be scanning at more than two different levels (each level providing radiation having a different energy profile).

In this embodiment, the object is irradiated in discrete bursts—in other embodiments the skilled person will realise that radiation levels can be varied gradually, or in a combination of bursts and gradual variation and the data collection signal processing should be amended accordingly (this is discussed in more detail below).

In some embodiments, the method 10 comprises sending detected information received in response to a burst from the detector regions before the next burst occurs. This helps to simplify signal processing.

The primary equation that governs X-ray attenuation in matter is $$I(E) = I_0(E)\exp\left(-\int_l \mu(E)dl\right) \quad (1)$$

where $I(E)$=intensity of radiation transmitted through the object at energy E, $I_0(E)$=intensity of radiation emitted by the source at energy E, $\mu(E)$=linear attenuation coefficient of object at energy E and l=line taken by the pencil beam of radiation through the object.

Figure 3:
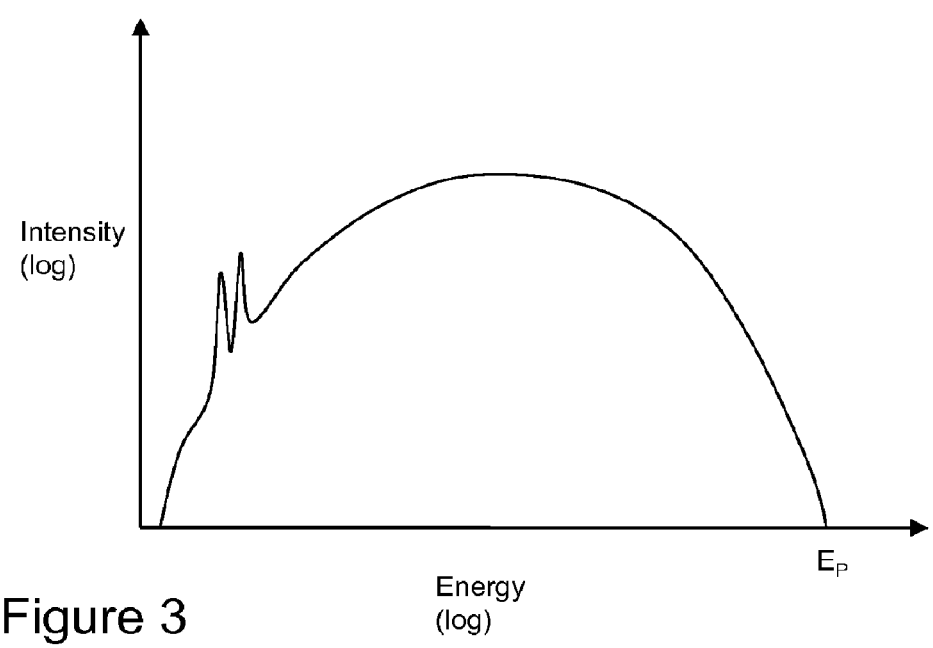
FIG. 3 graphically illustrates an output radiation profile from a radiation source used in an embodiment of the present invention.

The X-ray output from an X-ray linear accelerator is polychromatic having an energy distribution substantially as shown in FIG. 3. The maximum X-ray energy (Ep) results from those electron interactions in the target of the linear accelerator where all of the electron energy is transferred to a single X-ray photon. Typically, less than the full electron energy is transferred to a photon resulting in the broad range of X-ray energies in the X-ray beam. At low energy, the peaks shown in FIG. 3 are due to fluorescence interactions between the electrons and the target atoms so resulting in X-rays which are characteristic of the target material.

It is customary to use an integrating detector to measure the X-ray signal that is described in equation 1. In this case, the detected signal can be written as $$I_d = \int_0^{E_p} I(E)\left[1 - \exp\left(-\int_s \mu_d(E)ds\right)\right] \quad (2)$$

where $I_d$=detected signal, $\mu_d(E)$=linear attenuation coefficient of the detector material at energy E and s=path length of the X-ray beam through the detector.

It is therefore clear that $I_d$ retains no knowledge of the energy distribution of the incoming X-ray beam, only of the cumulative effect of all X-ray energies.

Figure 4:
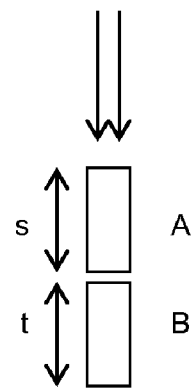
FIG. 4 schematically illustrates a detector arrangement according to an embodiment of the invention.

However, it can also be seen that unless the path through the detector material, s, is very large indeed, some energy will be transmitted through the detector (i.e. it will not have a 100% detection efficiency). Referring to FIG. 4, if a second detector, B, is placed at the output of the first detector, A, then the energy transmitted through the first detector has a chance of being absorbed in the second detector. In this case we can write:

$$I_{dB} = \int_0^{E_p} I(E)\exp\left(-\int_s \mu_{dA}(E)ds\right)\left[1 - \exp\left(-\int_t \mu_{dB}(E)dt\right)\right] \quad (3)$$

where $I_{dB}$=intensity recorded in detector B, $\mu_{dA}(E)$=linear attenuation coefficient of detector A material at energy E, $\mu_{dB}(E)$=linear attenuation coefficient of detector B material at energy E and t=path taken by the X-ray beam through detector B.

Inspection of equation 3 shows that the energy spectrum that is incident on detector B is not the same as the energy spectrum that is incident on detector A. Therefore, detector A can be thought to have retained some energy information even though the integrated output alone is not sufficient to tell what this energy information is. The same is true of detector B.

In this invention, it is recognised that the measurements that are produced by detector A and detector B are spatially and temporally correlated and that the ratio of the intensity recorded in detector A to that recorded in detector B will necessarily provide some information about the energy distribution of the incident X-ray beam, i.e.

$$\frac{I_{dA}}{I_{dB}} = f\{I(E)\} \quad (4)$$

where $f\{\ \}$=function operator.

It can further be seen through inspection of equation (1), that the ratio of detector measurements also includes a factor that is due to attenuation in the object.

Three object parameters will affect the ratio of detectors (equation 4) and these are the linear attenuation coefficient of the object, $\mu(E)$, the path l taken by the X-ray beam through the object and the energy distribution of the primary beam, Io(E). In this situation, there are three unknowns and two measurements and therefore it is impossible to uniquely determine a value for the three object unknowns.

In another aspect of this invention, it is recognised that if the X-ray linear accelerator can be tuned to produce more than one primary beam distribution then two pairs of detector results can be collected, one with a lower energy primary beam distribution, $I_{dA}$(lo) and $I_{dB}$(lo), and one with a higher primary beam energy distribution, $I_{dA}$(hi) and $I_{dB}$(hi). There are now four measurements with the same three unknowns and it is therefore possible to determine a mathematically unique solution. This solution can be determined using an appropriate numerical technique such as least squares minimisation. In other embodiments any other similar or suitable numerical technique can be used as an alternative or in combination.

The present invention is concerned with high energy scanning. At low energies (for example most medical scanners), the photo-electric effect is a mechanism by which X-rays interact with matter within objects being scanned. In contrast, the present invention is concerned with much larger X-ray source energies—namely, lower energy primary beam distribution mentioned above has a peak value of 500 keV or above (and the higher energy beam has a value higher than this). The predominant mechanism governing interactions of radiation within matter at these energies is Compton scattering.

The attenuation in matter of X-rays affected by the photo-electric effect shows a dependence proportional to $Z^4$ (where Z=atomic number). In contrast, Compton scattering produces a $Z^1$ dependence. Some Compton scattering is also present at low energies.

The detector regions of the present invention are configured such that in the front detector, there is an approximately $Z^4$ dependence arising from a combination of the photo-electric and Compton scattering effects. The second, rear detector has a $Z^1$ dependence. As a result there are significantly different considerations compared to low energy X-ray scanning, due to the different physical laws governing the interaction of matter. The inventor has realised that for high energy X-ray scanning applications, the front and rear detectors in the claimed arrangement are governed by different physical laws with regards to their interaction with high energy radiation. As a result of the different physical relationships, different detector arrangements are required, relative to low energy X-ray scanners. Accordingly, a first detector is specified as being at least 2 mm thick, whilst the second detector is specified as being at least 5 mm thick. Also, different signal processing is required to account for the combination of the photo-electric effect and Compton scattering occurring at the first detector, and the predominantly Compton scattering effect at the second detector. As a result conventional cargo scanners do not have a dual detector region arrangement as specified in this invention.

The detector arrangement for use in a scanning system of this type (i.e. the system comprises a radiation source arranged to irradiate an object to be scanned, wherein the detector arrangement is arranged to detect radiation after it has interacted with or passed through the object in order to scan the object) may be a stacked detector, wherein the detector arrangement comprises a first detector region arranged to detect radiation and a second detector region arranged to detect radiation wherein the second detector region is arranged to receive radiation that has passed through the first detector region. In this example the first detector region is positioned between the object to be scanned and the second detector region. The first detector region and the second detector region are configured to detect a predetermined amount of radiation relative to each other—in this example, the first detector region and the second detector region are configured to detect substantially the same amount of radiation as each other—in this example this is achieved by configuring the lengths s, t of the detectors A, B.

Both or each of the first detector and the second detector may comprise a linear detector array.

An example of the data that can be recorded using a system with stacked detectors as exemplified in this invention (and as shown in FIG. 4) is given in FIGS. 5 to 8. In these figures, I is the total integrated intensity of radiation detected, i.e. the sum of the intensity at the first detector, A, and the second detector, B. F/R is a measure of the ratio of intensity of radiation detected at the front and rear detectors. L/H is a measure of the ratio of intensity of radiation detected at low and high source energy profile.

At lower energies, the front detector absorbs most of the radiation which reaches it. As a result there is a good distinction relative to the absorption at the rear detector between high Z and low Z objects, where Z=atomic mass. Therefore the ratio, F/R provides particularly useful information at low energies.

At higher energies, the L/H ratio provides good distinction between high Z and low Z objects. Therefore the ratio, L/H provides particularly useful information at high energies.

In combination these two ratios help to provide comprehensive information across the energy spectrum.

Figure 5:
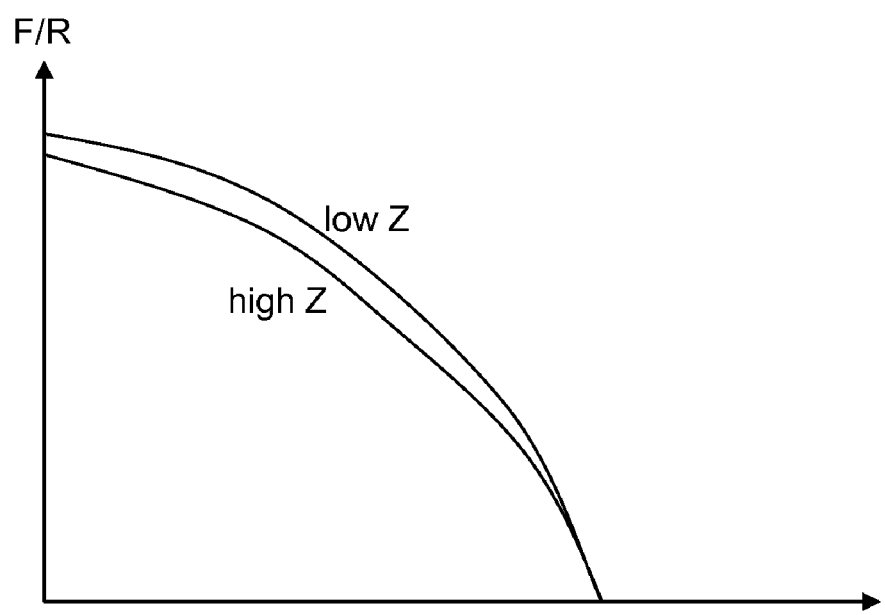
FIG. 5 is a graph illustrating different characteristics of high and low atomic mass objects as seen by the scanning system of an embodiment of this invention.
Figure 6:
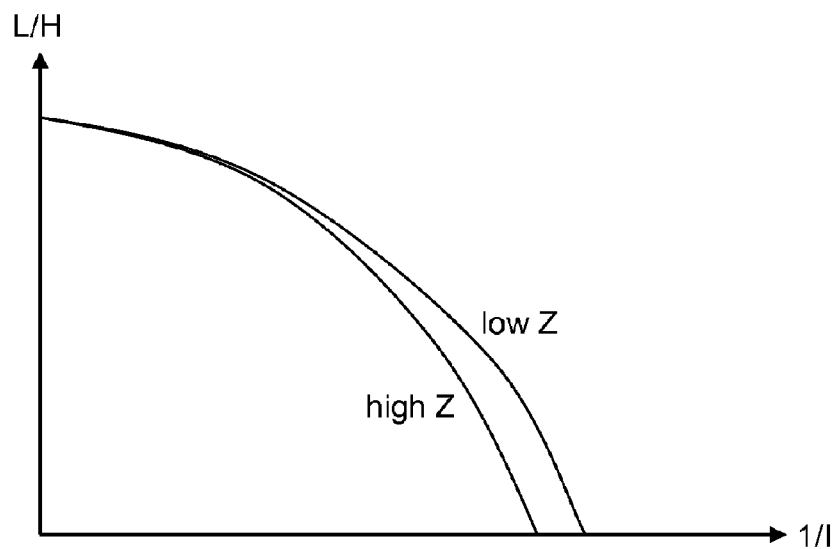
FIG. 6 is a graph illustrating different characteristics of high and low atomic mass objects as seen by the scanning system of an embodiment of this invention.
Figure 7:
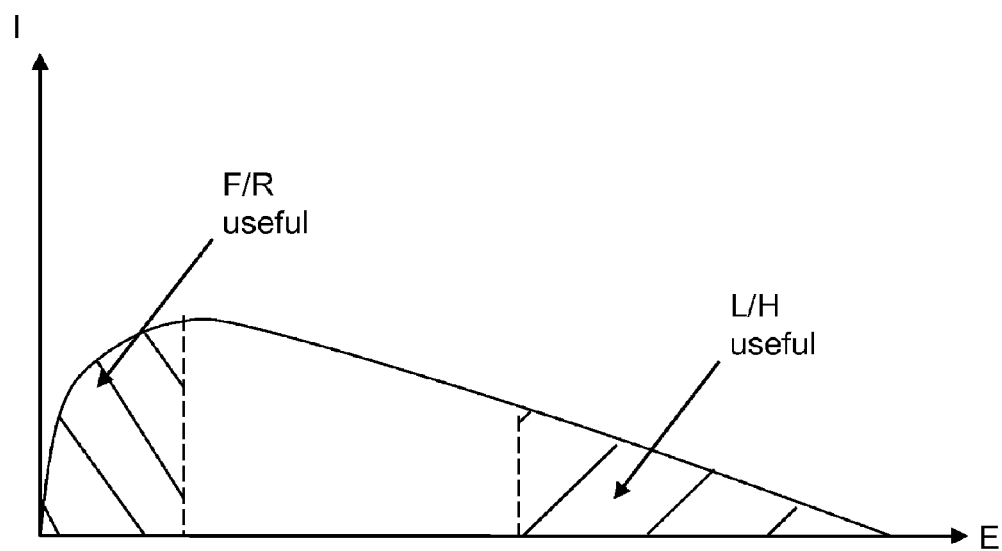
FIG. 7 is a graph illustrating the change in response relative to the energy of received radiation.
Figure 8:
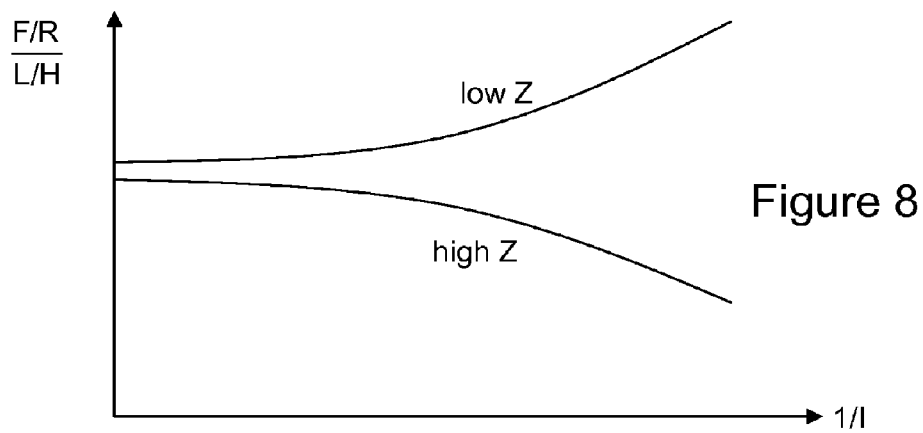
FIG. 8 is a graph illustrating the change in response relative to intensity of received radiation for high and low atomic mass objects.

FIG. 8 shows the percentage difference between the two curves in FIGS. 5 and 6. As a guide the difference between the intensity ratios at low and high energies can be as large as 10 percent. Given that the noise floor in a good quality detection system should be on the order of 10 parts per million, a several percent change in intensity ratio is very measureable.

Figure 9:
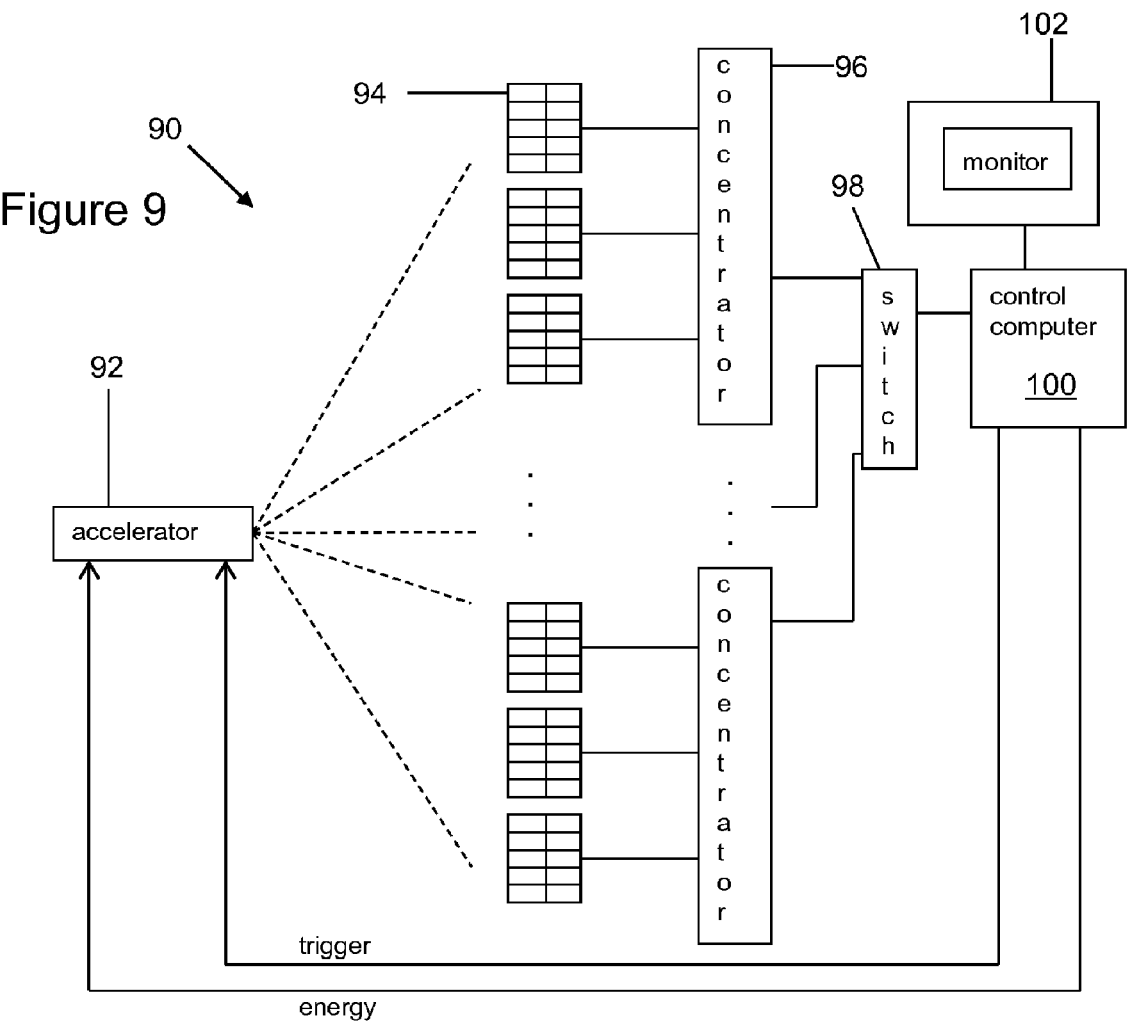
FIG. 9 schematically shows a data acquisition system for use with this invention.

In one embodiment, a suitable data acquisition system 90 for use with the scanning system is shown in FIG. 9. Here a pulsed X-ray accelerator 92 has two inputs, Trigger and Energy. X-rays from the accelerator 92 pass through the object under inspection and intercept sensor arrays 94 that have front and rear sensor elements. The analogue signal is integrated and converted to a digital form prior to transmission to a set of concentrator cards 96 which format Ethernet packets that contain the digitised sensor data. These Ethernet packets are passed from each Concentrator card back through an Ethernet Switch 98 to a controlling computer 100 where they are formatted into lines in an image which are then displayed on a human readable monitor 102. Each line in the image corresponds to one accelerator pulse worth of sensor data. Of course, other data acquisition system architectures are quite workable and will be apparent to the skilled person, and FIG. 9 is presented as an example of good practice in data acquisition design.

Figure 10:
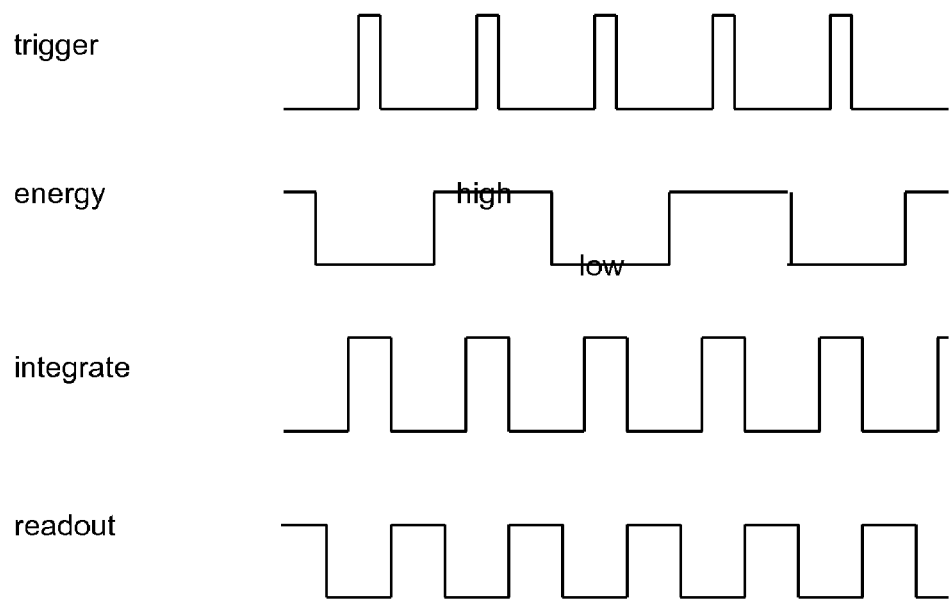
FIG. 10 illustrates a timing pattern for the data acquisition system of FIG. 9 in one embodiment.

FIG. 10 presents an example of a timing diagram for acquisition of quad-energy X-ray data. A trigger pulse trigger switching of the energy level of the radiation source between its high and low levels. Detection events are integrated at each detector co-ordinated in time with the high and low energy states, and readout from each detector occurs prior to the next integration event.

In some embodiments it is advantageous to use an offset staggered row detector to improve scanning speed, to increase detection efficiency and to provide improved spatial correlation between the high and low energy X-ray measurements. This may be done to achieve Nyquist sampling rates for example.

In some embodiments, it can be advantageous to utilise non-periodic pulse sequences of radiation from the source in order to assist in reducing dose rates and to provide superior object penetration performance.

Figure 11:
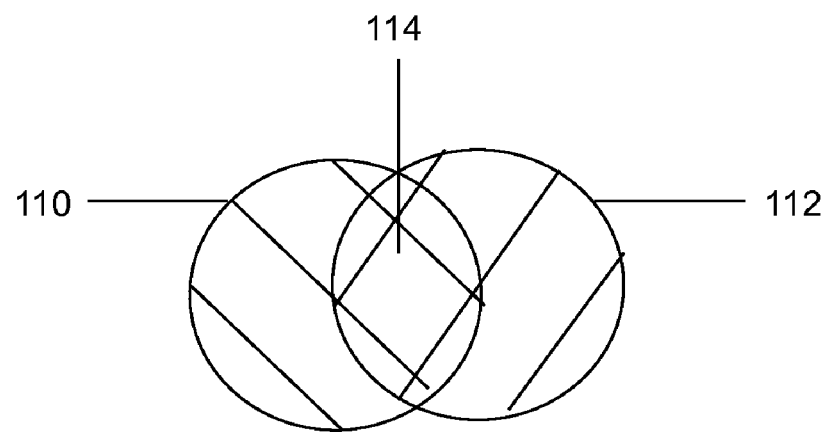
FIG. 11 is a representation of overlapping objects which can be distinguished using this invention.

In a further aspect of this invention, it is observed that the analysis provided in equations 1 through 4 above relates to a single homogeneous object. In a real object, there are often multiple objects which may overlap in the image. An example of overlapping objects is shown in FIG. 11. Here a first object 110 is partially overlapped by a second object 112. In each case, the overall shape of the objects is visible to the human eye, even in the overlap region 114. In this invention it is claimed that automated image processing methods can be used to segment the projected quad-energy X-ray image to resolve the materials characteristics of the region to the left of the first object 110 and the region to the right of the second object 112. This information about the objects 110 and 112 can then be used to analyse the overlapping area 114. Knowing the beam quality, thickness and attenuation coefficient of the first object 110 and the thickness and attenuation coefficient of the second object 112, it is possible to calculate the expected intensity that should be detected in the overlap region using the following equation:

$$I(E) = I_0(E)\exp\left(-\left\{\int_0^{t_1}\mu_1(E)dl + \int_0^{t_2}\mu_2(E)dl\right\}\right) \quad (5)$$

where $t_1$=thickness of the first object 110, $\mu_1(E)$=attenuation coefficient of the first object 110 at energy E, $t_2$=thickness of the second object 112 and $\mu_2(E)$=attenuation coefficient of the second object 112 at energy E. Note that the detected values, $I_{dA}(lo)$, $I_{dB}(lo)$, $I_{dA}(hi)$ and $I_{dB}(hi)$ are then determined through equations 3 and 4. The measured values can then be compared to the associated calculated values to ensure that noting else is present in the overlap region 114.

It is noted that the techniques discussed here can be extrapolated to further more complex situations. For example, an X-ray source could be developed to operate at more than two beam energies and more than two detector layers could be assembled to give finer still sampling of the energy distribution of the transmitted X-ray signals. The data analysis methods are the same, but there are further measurements of the same number of unknowns and it is therefore in principle possible to generate a better determined solution.

In an alternative embodiment, metal filter layers could be interposed between the detector elements in order to further shape the X-ray spectrum. This method is not recommended since no signal is recorded from the metal filter layer and the net result is a higher dose image than when an active detector is used as a filter for the equivalent purpose.

Various modifications may be made to this invention without departing from its scope (as defined by the claims). The high and low energy x-rays may be sent in a different order, e.g. low energy, then high energy.

Different ratios may be calculated with the four elements of information. The ratio described in the above example: $(A/B)_{lo}/(A/B)_{hi}$ is particularly useful since it takes away the need for calibration of the detectors. Other unique ratios which can be used are $A_{hi}/A_{lo}$, $A_{hi}/B_{lo}$, $A_{lo}/B_{hi}$, $A_{hi}/B_{hi}$, $A_{lo}/B_{lo}$. These are unique ratios—$B_{hi}/A_{lo}$ can be used but offers no advantage above $A_{lo}/B_{hi}$ since it is merely its inverse—similarly for other ratio examples.

In some embodiments more than two detector regions may be provided and more than two radiation energy levels may be used for irradiation of the object. For example instead of two, three or four or five or six or any other suitable number of energy levels may be used.

Exactly the same detector array principle can be used with other imaging probes including thermal neutrons and fast neutrons which can provide additional diagnostic benefit.

It will be clear to the skilled person that different peak values for the lower energy profile and/or the higher energy profile may be used within the bounds specified by the claims. For the example the lower profile peak energy value may be 4 MeV, and the higher profile peak energy value may be 7 or 8 MeV.

I claim:

1. A scanning method for scanning an object comprising:
providing a first detector region having a thickness of at least 2 mm and a second detector region having a thickness of at least 5 mm wherein the second detector region is arranged to receive radiation that has passed through the first detector region;
irradiating the object with a first high energy radiation profile;
detecting the first high energy profile radiation after it has interacted with or passed through the object in order to provide information relating to the object, wherein detecting the first high energy profile radiation comprises:
    detecting the first high energy profile radiation at the first detector region;
    receiving the first high energy profile radiation that has passed through the first detector region at the second detector region;
    detecting the first high energy profile radiation at the second detector region;
irradiating the object with a second low energy radiation profile detecting the second low energy profile radiation after it has interacted with or passed through the object in order to provide information relating to the object, wherein detecting the second low energy profile radiation comprises:

detecting the second low energy profile radiation at the first detector region;

receiving the second low energy profile radiation that has passed through the first detector region at the second detector region;

detecting the second low energy profile radiation at the second detector region;

wherein the first detector region is positioned between the object and the second detector region; and calculating a ratio, $(A/B)_1/(A/B)_2$ in order to determine information relating to the object based upon said ratio, wherein A is indicative of an amount of radiation detected at the first detector region, B is indicative of an amount of radiation detected at the second detector region, $(A/B)_1$ is a ratio of the first high energy profile radiation detected at the first detector region relative to first high energy profile radiation detected at the second detector region, and $(A/B)_2$ is a ratio of the second low energy profile radiation detected at the first detector region relative to second low energy profile radiation detected at the second detector region.

2. The method of claim 1 comprising determining said information relating to the object by inputting information from the first detector region and the second detector regions relating to the first high energy profile radiation and second low energy profile radiation into a least squares minimization technique to obtain information relating to the object.

3. The method of claim 1 comprising irradiating and detecting the first high energy profile radiation before the second low energy profile radiation.

4. The method of claim 1 wherein irradiating the object comprises irradiating the object in discrete bursts.

5. The method of claim comprising sending detected information received in response to a burst from the detector regions before a next burst occurs.

6. The method of claim 1 comprising configuring the first detector region and the second detector region to detect a predetermined amount of radiation relative to each other.

7. The method of claim 6 comprising configuring the first detector region and the second detector region to detect substantially a same amount of radiation as each other.

8. The method of claim 6 comprising configuring any one or more of size, shape or material of the first detector region or second detector region so that the first detector region and the second detector region detect the predetermined amount of radiation relative to each other.

9. The method of claim 1 comprising providing a first detector including the first detector region and a second detector including the second detector region.

10. The method of claim 1 comprising irradiating the object with radiation at more than two energy profiles.

11. A scanning system for scanning an object comprising:

a variable energy level radiation source arranged to irradiate an object with radiation having a plurality of different energy profiles including a first high energy profile having a peak energy ranging from 1 MeV to 6 MeV and a second low energy profile having a peak energy ranging from 0.5 MeV to 3 MeV; and a detector arrangement arranged to detect radiation after it has interacted with the object, wherein the detector arrangement comprises a first detector region having a thickness of at least 2 mm and arranged to detect radiation and a second detector region having a thickness of at least 5 mm and arranged to detect radiation wherein the first detector region is positioned between the object and the second detector region, further comprising a controller wherein the controller is arranged to calculate a ratio, $(A/B)_1/(A/B)_2$ in order to determine information relating to the object based upon the calculated ratio, wherein A is indicative of an amount of radiation detected at the first detector region, B is indicative of an amount of radiation detected at the second detector region, $(A/B)_1$ is a ratio of a first profile radiation detected at the first detector region relative to first profile radiation detected at the second detector region, and $(A/B)_2$ is a ratio of a second profile radiation detected at the first detector region relative to second profile radiation detected at the second detector region.

12. The scanning system of claim 11 wherein the controller is further arranged to coordinate a timing of irradiation events such that detected information obtained in response to one of the irradiation events is sent from the first and second detector regions before a subsequent irradiation event occurs.

13. The scanning system of claim 11 wherein the controller is further arranged to determine information relating to the object based upon information from the first and second detector regions relating to the first profile radiation and second profile radiation.

14. The scanning system of claim 13 wherein the controller is arranged to determine information by inputting the information from the first and second detector regions relating to the first profile radiation and second profile radiation into a least squares minimization technique to obtain information relating to the object.

15. The scanning system of claim 11 comprising a plurality of detector arrays, each detector array comprising a first detector region and a second detector region.

16. The scanning system of claim 15 comprising a concentrator and switch arranged to coherently relay gathered information from the first and second detector regions.

17. The scanning system of claim 11 wherein the first detector region and the second detector region are configured to detect substantially a same amount of radiation as each other.

* * * * *